(12) United States Patent
Eisermann et al.

(10) Patent No.: US 7,341,601 B2
(45) Date of Patent: *Mar. 11, 2008

(54) WOVEN ORTHOPEDIC IMPLANTS

(75) Inventors: Lukas Eisermann, Memphis, TN (US); Eddie F. Ray, III, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/900,614

(22) Filed: Jul. 28, 2004

(65) Prior Publication Data

US 2005/0043733 A1 Feb. 24, 2005

Related U.S. Application Data

(63) Continuation of application No. 10/082,579, filed on Feb. 25, 2002, now Pat. No. 6,827,743.

(60) Provisional application No. 60/272,246, filed on Feb. 28, 2001.

(51) Int. Cl.
*A61F 2/44* (2006.01)

(52) U.S. Cl. .................................. 623/17.11

(58) Field of Classification Search ................ 606/151, 606/154, 157, 60, 62, 76, 77; 623/13.2, 13.12, 623/13.19, 23.53, 23.54, 23.57, 23.58, 23.59, 623/23.72, 23.73, 23.75, 23.76
See application file for complete search history.

(56) References Cited

U.S. PATENT DOCUMENTS

| | | | |
|---|---|---|---|
| 3,272,204 A | 9/1966 | Artandi et al. |
| 3,463,158 A | 8/1969 | Schmitt et al. |
| 3,710,789 A | 1/1973 | Ersek |
| 4,089,071 A | 5/1978 | Kalnberz et al. |
| 4,502,161 A | 3/1985 | Wall |
| 4,570,623 A | 2/1986 | Ellison et al. |
| 4,610,688 A | 9/1986 | Silvestrini et al. |
| 4,665,951 A | 5/1987 | Ellis |
| 4,728,329 A | 3/1988 | Mansat |
| 4,743,260 A | 5/1988 | Burton |
| 4,755,183 A | 7/1988 | Kenna |
| 4,772,287 A | 9/1988 | Ray et al. |
| 4,820,305 A | 4/1989 | Harms et al. |
| 4,834,755 A | 5/1989 | Silvestrini et al. |
| 4,883,486 A | 11/1989 | Kapadia et al. |
| 4,904,260 A | 2/1990 | Ray et al. |
| 4,917,700 A | 4/1990 | Aikins |
| 4,955,911 A | 9/1990 | Frey et al. |
| 4,990,163 A | 2/1991 | Ducheyne et al. |

(Continued)

FOREIGN PATENT DOCUMENTS

EP 0304305 2/1989

(Continued)

*Primary Examiner*—Anuradha Ramana
(74) *Attorney, Agent, or Firm*—Krieg DeVault LLP

(57) ABSTRACT

The present invention relates to orthopedic implants made from a mesh material. The mesh material can be treated in order to promote bone growth, to provide antibiotics, or to provide other beneficial treatment. Specific applications for the implants include, for example, a prosthetic ligament, a tension band, an interbody device, or a fixation device that extends across one or more joints or fractures.

24 Claims, 10 Drawing Sheets

U.S. PATENT DOCUMENTS

| | | | |
|---|---|---|---|
| 5,011,484 A | 4/1991 | Bréard | |
| 5,030,233 A | 7/1991 | Ducheyne | |
| 5,084,051 A | 1/1992 | Törmälä et al. | |
| 5,102,421 A | 4/1992 | Anspach, Jr. | |
| 5,108,395 A | 4/1992 | Laurain | |
| 5,141,522 A * | 8/1992 | Landi | 523/114 |
| 5,156,616 A | 10/1992 | Meadows et al. | |
| 5,157,111 A | 10/1992 | Pachence | |
| 5,171,273 A | 12/1992 | Silver et al. | |
| 5,180,393 A | 1/1993 | Commarmond | |
| 5,195,542 A * | 3/1993 | Gazielly et al. | 128/898 |
| 5,222,987 A | 6/1993 | Jones | |
| 5,344,421 A | 9/1994 | Crook | |
| 5,346,492 A | 9/1994 | Morgan | |
| 5,366,504 A | 11/1994 | Andersen et al. | |
| 5,376,118 A | 12/1994 | Kaplan et al. | |
| 5,380,328 A | 1/1995 | Morgan | |
| 5,397,359 A | 3/1995 | Mittelmeier et al. | |
| 5,405,391 A * | 4/1995 | Hednerson et al. | 623/17.15 |
| 5,441,508 A * | 8/1995 | Gazielly et al. | 606/151 |
| 5,443,483 A | 8/1995 | Kirsch | |
| 5,456,722 A | 10/1995 | McLeod et al. | |
| 5,496,372 A | 3/1996 | Hamamoto et al. | |
| 5,527,311 A | 6/1996 | Procter et al. | |
| 5,540,964 A | 7/1996 | Mallen | |
| 5,549,679 A | 8/1996 | Kuslich | |
| 5,609,634 A | 3/1997 | Voydeville | |
| 5,634,944 A | 6/1997 | Magram | |
| 5,674,295 A | 10/1997 | Ray et al. | |
| 5,681,310 A | 10/1997 | Yuan et al. | |
| 5,711,960 A | 1/1998 | Shikinami | |
| 5,721,049 A | 2/1998 | Marcolongo et al. | |
| 5,824,093 A | 10/1998 | Ray et al. | |
| 5,842,477 A * | 12/1998 | Naughton et al. | 128/898 |
| 5,906,828 A | 5/1999 | Cima et al. | |
| 6,022,376 A | 2/2000 | Assell et al. | |
| 6,031,148 A | 2/2000 | Hayes et al. | |
| 6,045,554 A | 4/2000 | Grooms et al. | |
| 6,066,175 A | 5/2000 | Henderson et al. | |
| 6,077,076 A | 6/2000 | Comfort | |
| 6,093,205 A | 7/2000 | McLeod et al. | |
| 6,113,640 A | 9/2000 | Törmälä et al. | |
| 6,121,172 A | 9/2000 | Marcolongo et al. | |
| 6,143,036 A | 11/2000 | Comfort | |
| 6,162,537 A * | 12/2000 | Martin et al. | 428/373 |
| 6,165,217 A * | 12/2000 | Hayes | 623/11.11 |
| 6,210,439 B1 | 4/2001 | Firmin et al. | |
| 6,267,772 B1 | 7/2001 | Mulhauser et al. | |
| 6,270,530 B1 | 8/2001 | Eldridge et al. | |
| 6,332,894 B1 | 12/2001 | Stalcup et al. | |
| 6,391,060 B1 | 5/2002 | Ory et al. | |
| 6,629,997 B2 * | 10/2003 | Mansmann | 623/14.12 |
| 2003/0078660 A1 | 4/2003 | Clifford et al. | |

FOREIGN PATENT DOCUMENTS

| | | |
|---|---|---|
| EP | 0353936 | 2/1990 |
| EP | 0507162 | 4/1991 |
| FR | 2612392 | 3/1987 |
| WO | WO 98/55053 | 12/1998 |
| WO | WO 99/47082 | 9/1999 |
| WO | WO 99/62439 | 12/1999 |

* cited by examiner

WOVEN ORTHOPEDIC IMPLANTS

CROSS-REFERENCE TO RELATED APPLICATION

This application is a continuation of U.S. patent application Ser. No. 10/082,579 filed Feb. 25, 2002 now U.S. Pat. No. 6,827,743, which claims the benefit of U.S. Provisional Application Ser. No. 60/272,264 filed Feb. 28, 2001, which is hereby incorporated by reference in its entirety.

FIELD OF THE INVENTION

The present invention relates to orthopedic implants, and more particularly, to orthopedic implants made from metal mesh material.

BACKGROUND OF THE INVENTION

In order to stabilize a bone or bony segment, such as the spinal column or a fractured bone, it is known to secure a rigid metal plate, rod, or other rigid support to the bone portions comprising the bone segment. Such rigid supports are useful, for example, in stabilizing and immobilizing a fracture of the bone since the support can be secured to the bone portions on each side of the fracture.

With respect to the spinal column, various techniques require access to an intervertebral disc space. Examples of such techniques include the repair of a herniated disc or the insertion of one or more interbody fusion devices, interbody spacers, or artificial discs. In order to access the disc space, one or more spinal ligaments and bony tissue may have to be severed or at least partially resected to allow insertion of surgical instruments and implants into the disc space. Posterior or anterior rigid metal supports can be used to stabilize the spinal column after these techniques are completed. Furthermore, devices inserted in the disc space can be made from rigid, inert metal material, bone material, or polymeric material.

It has been stated by some writers that the use of rigid metal plates to immobilize bones and bony portions can have certain drawbacks since such a plate will be in close contact with the vasculature and tissue along the bone. For example, it has been stated that the potential for screw back out and plate loosening creates a risk for erosion of the vasculature and the surrounding tissue. It has also been stated that rigid metal plates could bend in an undesired manner or break due to compressive loading and fatigue of the metal. A fracture or undesired bend in the plate could erode the tissue and vasculature surrounding the plate. Metal plates could also cause stress shielding.

In situations where spinal fusion is desired, it is known to place rigid metal supports in the disc space. Bone growth material can be placed in these supports. However, in the case of metal supports, openings must be formed through the walls of the support to accommodate fusion. In order to maintain the ability of the support to resist the in-vivo loads, these holes must be limited in number and in size so that the implant retains its structural integrity, providing relatively large regions on the implant which have no bone ingrowth.

Improved orthopedic implants that avoid at least some of the problems associated with rigid supports are therefore needed. The implants should be resistant to fatigue, stress shielding and the loads that are typically applied to the bone or bony segment. What is further needed are improved orthopedic implants to repair or replace resected ligaments or bony tissue, while the implant promotes bone ingrowth, fusion and/or healing. Also needed are improved orthopedic implants that have a profile that is as low as possible to avoid the potential complications associated with the vasculature and other tissue in this anatomic region. In addition, it is desirable to have orthopedic implants that avoid the complications with rigid supports. The present invention is directed toward meeting these needs, among others.

SUMMARY OF THE INVENTION

The present invention relates to orthopedic implants made at least partially from metal mesh material to form an orthopedic implant. In a preferred form, the metal mesh material includes metal wire of suitable tensile strength and which is not subject to substantial creep deformation or in vitro degradation. In a further preferred form, the mesh material can be treated in order to promote bone growth, to deliver pharmaceutical agents, such as antibiotics, anti-inflammatories or other beneficial treatments.

In one form, it is contemplated that the wire used to form the mesh can be made from stainless steel, cobalt-chrome alloy, titanium, titanium alloy, or nickel-titanium shape memory alloys, among others. It is further contemplated that the metallic wire can be interwoven with non-resorbable polymers such as nylon fibers, carbon fibers and polyethylene fibers, among others, to form a metal-polymer composite weave. Further examples of suitable non-resorbable materials include DACRON and GORE-TEX. In preferred embodiments, the mesh includes one or more reinforcing elements or members attached to the wires. Specific applications for the implants of the present invention include, for example, a prosthetic ligament, a tension band, an interbody fusion or spacer device, or an external fixation device that extends across one or more joints, bone defects or fractures of a bony segment or bone.

It is contemplated that the implants of the present invention can be constructed from one or more layers of mesh material. It is further contemplated that multiple layers of mesh material can be stacked one on top of another and attached by sewing, suturing, rivets, grommets, an adhesive, or other attachment system. It is also contemplated that the mesh layers can be seeded in vitro with bone forming cells, such as osteoblasts, and/or with growth factors. Multiple layers of osteoblast-seeded mesh may be stacked on top of one another and further allowed to or encouraged to proliferate. Due to the attachments formed between cells, a biologic metal-bone composite structure is created in-vitro. Bone growth material or bone material can also be placed between or within the mesh layers.

In one specific form of the present invention, layers of biologic metal-bone composite material can be stacked on top of each other to form a relatively rigid plate for immobilizing fractures or adjacent bone sections. In another form, the mesh material is used to form an annulus repair device. In a further form of the invention, one or more stiff rods may be attached to or placed between the layers of the woven material to act as reinforcing spars. The reinforced implant can be used in lieu of a fixation plate, for example, to wrap around a long bone to immobilize a fracture.

In another form of the present invention, the mesh material can be used to form a hollow implant having application as an interbody fusion device or interbody spacer. It is also contemplated that the mesh material can be seeded in vitro with osteoblasts, and/or formed with bone growth material or bone material between or within the layers. The hollow implant can act as a bag or container for holding material that allows the implant to resist compressive loads. Some examples of curable materials include those that are flowable above the body temperature, but solidify or otherwise cure in vivo to form a rigid core in the bag. Other examples of curing materials include polyarcylate, polymethacrylate, poly(methyl)methacrylate, calcium sulfate, various forms of calcium phosphate, and liquid silicone. Bone graft, hydrogel, or other non-curable material could be placed in the hollow interior. In a further form, the implant could be formed around a solid body made from bone or metal, for example.

In one embodiment, the hollow implant is in the form of a bag that has a hollow interior, an open end and an opposite closed end. The bag can have reinforcing fibers that extend through the hollow interior across at least the internal diameter of the bag. The bag can be flexible; for example, the bag can be collapsed much like a deflated balloon. The collapsed or smaller bag would facilitate surgical implantation at the targeted treatment site. The bag may be filled with a curing material under sufficient pressure in its liquid state to tension the reinforcing fibers and expand the bag to a desired volume either prior to or more preferably after implantation. Once the material cures, residual tensile stresses left in the reinforcing fibers apply compressive stress to the cured matrix material, thereby modulating the bulk mechanical properties of the structure.

In other embodiments, the mesh material forms a hollow implant that has an injection port through which bone growth material or other curing material can be injected. Once filled with material, the injection port can be closed by sutures, staples, adhesive, caps, and the like. Alternatively, the port can be self-sealing. In one specific application, the hollow implant is an interbody cage or spacer is insertable into an intervertebral disc space.

The mesh material of the present invention may be modified in a number of ways, including electrochemical surface modifications, coating applications and thermal treatments. For example, the mesh material can be anodized, can be thermally hardened, can have interwoven collagen material, can have collagen molecules immobilized to its surface, can be coated/impregnated with an elastomer, adhesive or a therapeutic agent, or can have alternating strands of metal wires and demineralized bone matrix or collagen. The alternate weave pattern may be used to adsorb or otherwise attach bone morphogenetic proteins, antibiotic agents or other therapeutic or beneficial molecules.

These and other aspects, forms, embodiments, features and advantages of the present invention will be apparent from the following description of the illustrated embodiments.

DESCRIPTION OF THE ILLUSTRATED EMBODIMENTS

For the purposes of promoting an understanding of the principles of the invention, reference will now be made to the illustrated embodiments and specific language will be used to describe the same. It will nevertheless be understood that no limitation of the scope of the invention is thereby intended. Any such alterations and further modifications of the invention, and any such further applications of the principles of the invention as illustrated herein are contemplated as would normally occur to one skilled in the art to which the invention relates.

The present invention relates to orthopedic implants made from metal material forming a mesh from which an implant can be fabricated. In a preferred form, the metal material includes metal wire or fiber of suitable tensile strength and which is not subject to substantial creep deformation or in vitro degradation. Preferably, the wire is of such size and/or material that the implant is flexible yet inelastic. It is contemplated that the metal mesh can be formed by weaving or knitting the wires into the desired pattern, or by attaching the wires to one another in the desired pattern by welding, thermal bonding, electrochemical adhesion, adhesive, or other attachment process.

Figure 1A:
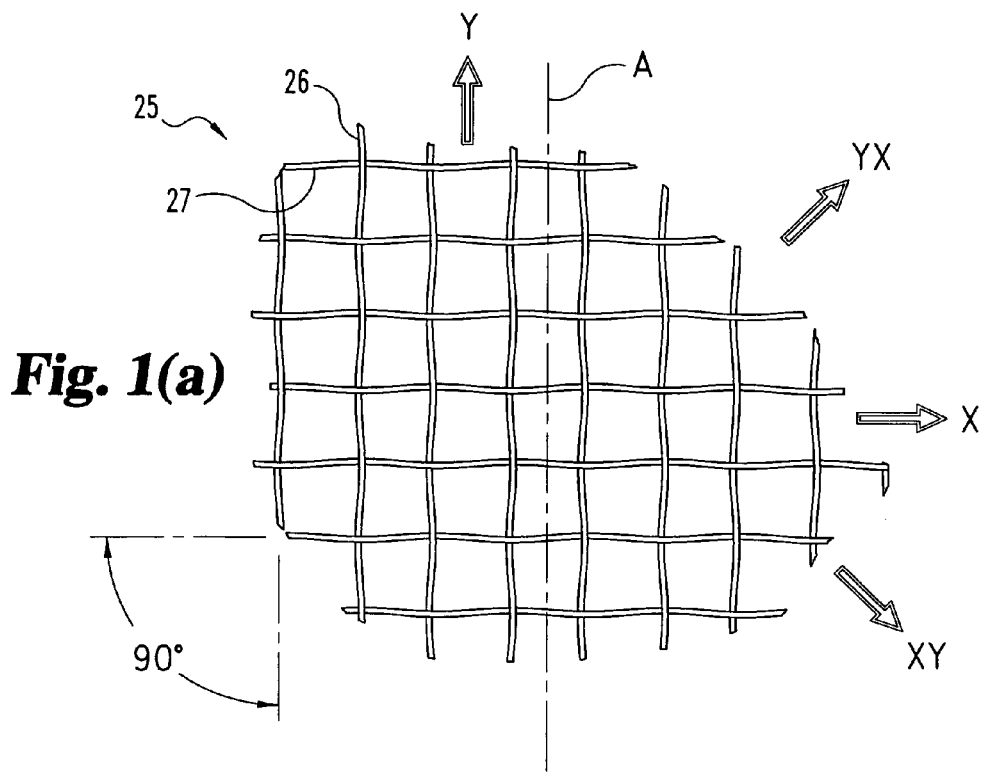
FIGS. 1(a), 1(b), 1(c), and 1(d) illustrate various weave patterns for mesh layers used to construct implants according to various embodiments of the present invention.

As shown in FIG. 1(a), a number of small diameter wires 26, 27 can be woven, knit, or attached in any number of patterns to form a metal mesh member 25 from which an implant according to the present invention can be made. In FIG. 1(a) the weave pattern of wires 26, 27 is substantially orthogonal in the x-y directions. Wires 26, 27 form mesh member 25 with a rectangular grid-like pattern that has similar tensile properties in both the x and y directions. It is contemplated that the implant made from mesh member 25 can be oriented such that the wires in either the x-direction or the y-direction extend along the central axis A of the bone member(s) to which the implant is to be attached.

Figure 1B:
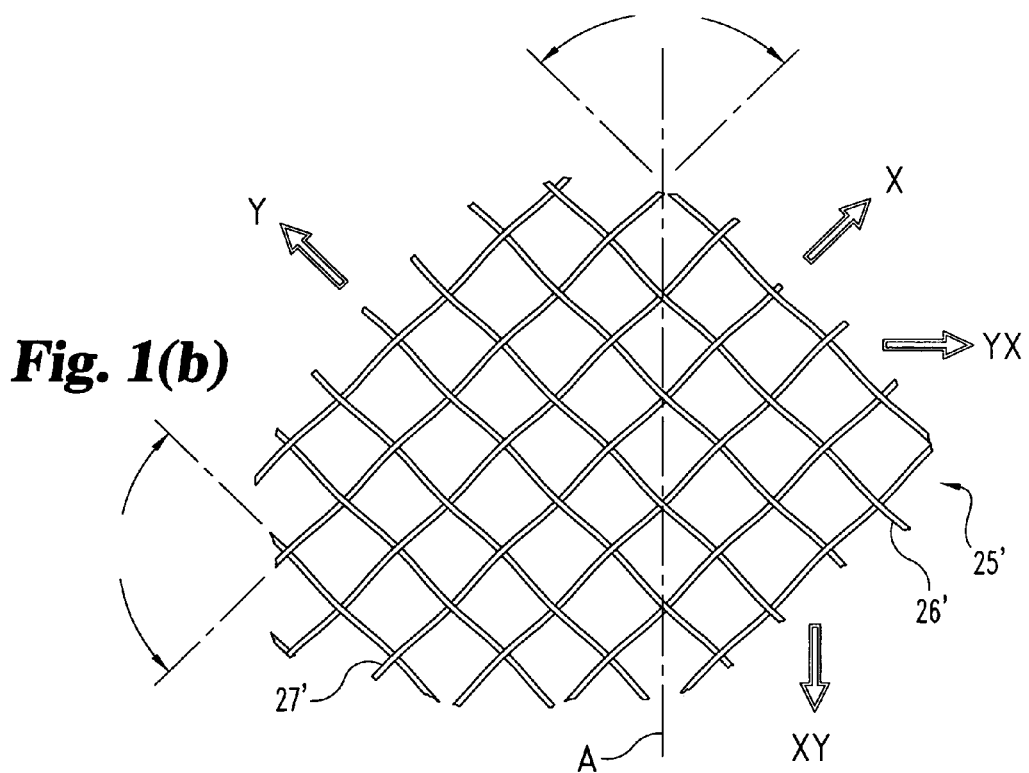
Figure 1C:
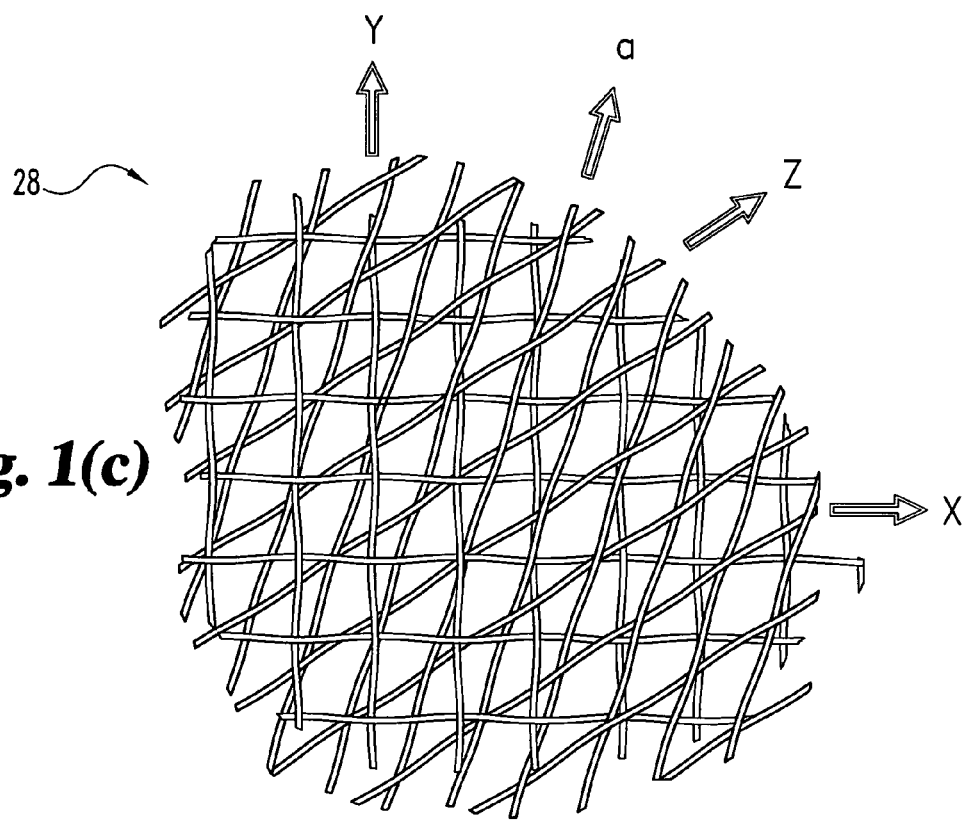
Figure 1D:
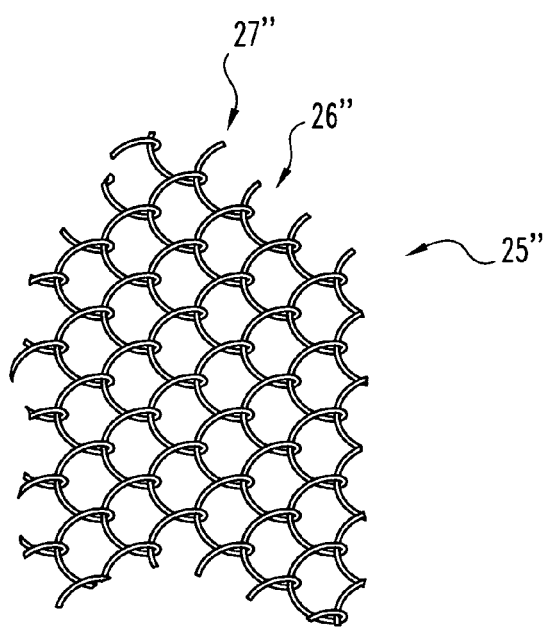

As shown in FIG. 1(b), the wires 26', 27' may also be non-orthogonal relative to one another and/or non-orthogonal relative to the central axis A of the bone member(s) to which the implant is to be attached. This allows the implant made from mesh member 25' to have force-resistance properties that are varied along differing axes in order to enhance the implant's resistance to various forces. Thus, it is contemplated that the angle α and the angle β can each be any angle selected from the range between 0° and 180°. Furthermore, it is possible to utilize more than two wire directions for forming the weave. It is further contemplated that a mesh 28 could be formed that has wires extending along multiple weave axes x, y, a, and z as shown in FIG. 1(c). In this form the mesh member resembles a three dimensional structure having devised dimensions in width, height and depth along the X, Y, and Z axis respectively. FIG. 1(d) depicts a weave that utilizes wires 26", 27" which are curled, rather than straight to form mesh 25".

Figure 2A:
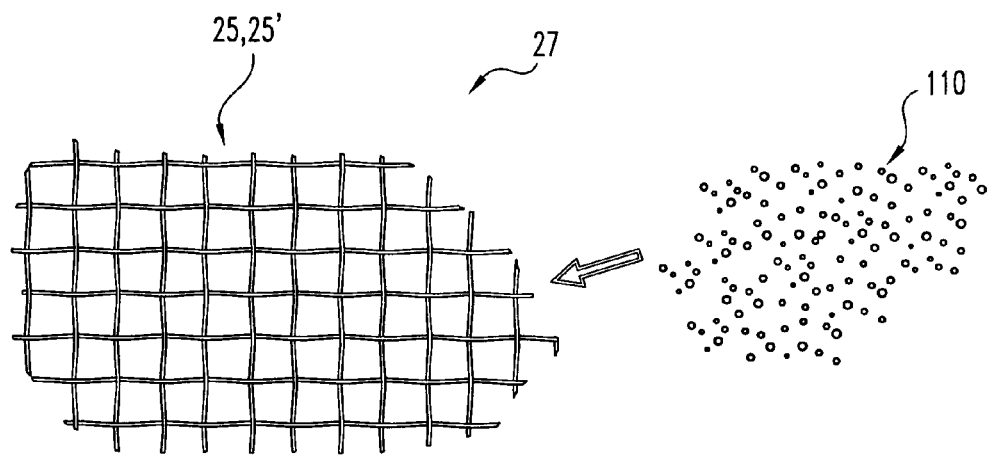
FIGS. 2(a), 2(b), and 2(c) illustrate various steps in forming mesh layers and base members used to construct implants according one embodiment of the present invention.
Figure 2B:
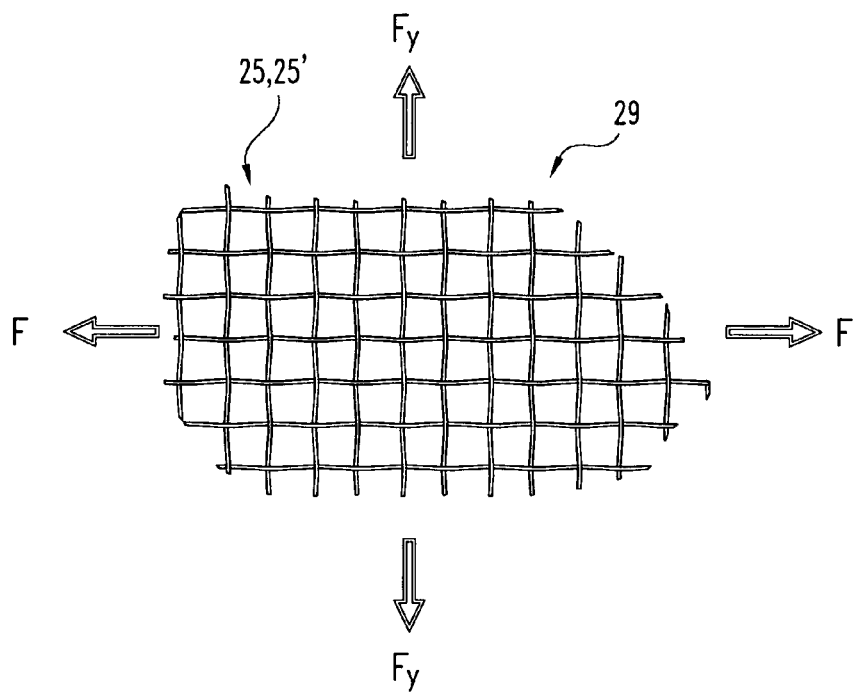
Figure 2C:
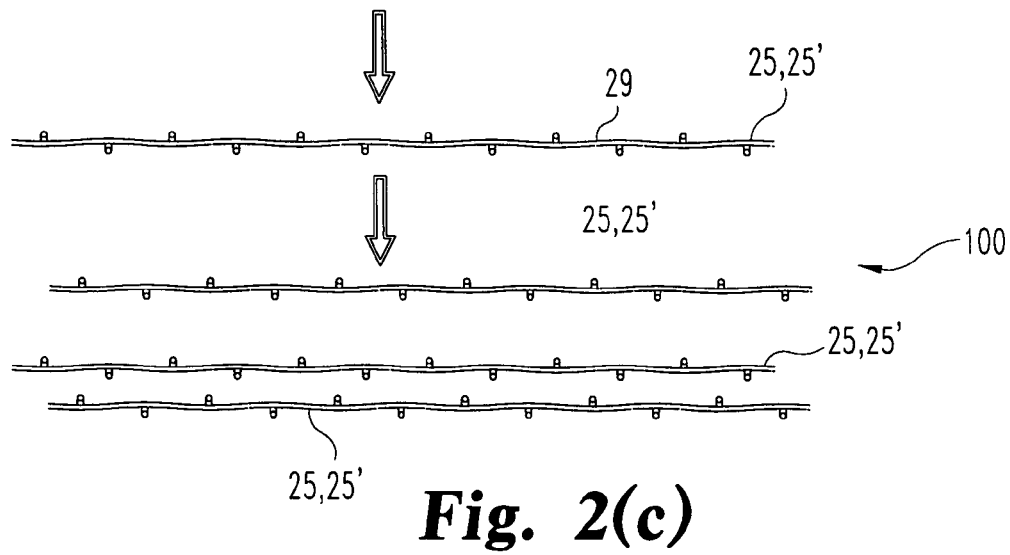

FIGS. 2(a) through 2(c) illustrate various steps in the method of forming a base member 200 using mesh members 25, 25', 25" and 28. As shown in FIG. 2(a), a mesh member 27 having one of the weave patterns discussed above is provided. In one preferred form, the mesh member 27 includes cells 110 such as osteoblasts that are injected or seeded onto the mesh in vitro. In order to encourage cell proliferation, the seeded mesh member 29 can be suspended in a medium receptive to cell growth and concurrently subjected to tensile loading as shown in FIG. 2(b). Tensile forces that are applied to mesh member 29 in the x and y direction illustrated as $F_x$ and $F_y$, respectively, have a range of load and duration of application that creates an environment conducive to osteoblast proliferation, maturation, cell adhesion, and calcification. As shown in FIG. 2(c), two mesh members 29 are then placed one on top of another in order to form base member 100 from which an implant can be fabricated. These multiple layers can be secured to one another by grommets, sewing, knitting, interweaving, suture, applying an adhesive, riveting, thermal bonding, or other technique. Preferably, the multiple layers are secured to one another by encouraging the seeded cells to proliferate and attach to one another. The desired shape for the implant is cut out and/or pressed or molded into a desired configuration from the base member 100 either before or preferably after seeding the layers with living cells.

It is contemplated that multiple layers of orthogonal mesh members 25, non-orthogonal mesh members 25', or combinations of orthogonal/non-orthogonal mesh members 25, 25', 25" and 28 can be stacked one upon another. The properties of each layer and the properties between the various layers can be varied in order to modulate the properties of the implant in various directions and in various locations. The implant can be a laminated construct having differing plies or layers. This allows the properties of base member 100 to be varied in specific regions for any number of purposes, such as to provide extra reinforcement in highly loaded regions, allow for a specific stress-strain response pattern, or to provide predetermined failure locations on the implant.

The present invention contemplates that various materials may be used for the metal wire used in the mesh members 25, 25', 25" and 28. Examples of such materials include stainless steels, cobalt chrome alloys, titanium, titanium alloys, and nickel titanium. It is further contemplated that the metal wires forming mesh members 25, 25', 25" and 28 can be interwoven with non-metallic materials such as nylon fibers, carbon fibers, fibers made from collagen strands, or polyethylene fibers, for example. In a preferred embodiment the selected materials provide a radiopaquic implant.

The wire used to form mesh members 25, 25', 25" and 28 can be modified through a number of processes, such as electrochemical surface modifications, coating applications, thermal treatments and so forth. For example, mesh members 25, 25', 25" and 28 can be made from a titanium wire and subsequently anodized. Another surface modification that is contemplated is to provide collagen immobilized to the surface of mesh members 25, 25', 25" and 28. Other treatments contemplate that mesh members 25, 25', 25" and 28 can be thermally treated before and/or after weaving. Mesh members 25, 25', 25" and 28 can also be coated or impregnated with an elastomer such as silicone or polyurethane or a bone cement.

In addition to in vitro seeding of osteoblasts, other treatments for the mesh members 25, 25', 25" and 28 are contemplated that also provide an implant that allows for bone ingrowth and regeneration of bony tissue. For example, in one embodiment the mesh members 25, 25', 25" and 28 are provided with alternating strands of metal wire and demineralized bone matrix. In another embodiment, mesh members 25, 25', 25" and 28 are smeared or coated with an osteoinductive bone paste, such as OSTEOFIL. In another embodiment, mesh members 25, 25', 25" and 28 have alternating strands of metal wires and collagen, and the mesh members 25, 25', 25" and 28 are subsequently soaked in a pharmacological agent such as recombinant human bone morphogenic protein, antibiotic agents, or other similar material. Still other embodiments contemplate no treatment is provided on mesh members 25, 25', 25" and 28.

Several layers of mesh members 25, 25', 25" and 28 can be stacked on top of another to form base member 100, which is then cut or molded into the desired shape for use as a bone plate, ligament, annulus repair device, intervertebral cage or interbody spacer, or fracture immobilization device. The desired geometry of the implant can be cut from base member 100 using any number of cutting processes appropriate to the combination of materials and geometries used in the implant design.

Figure 3:
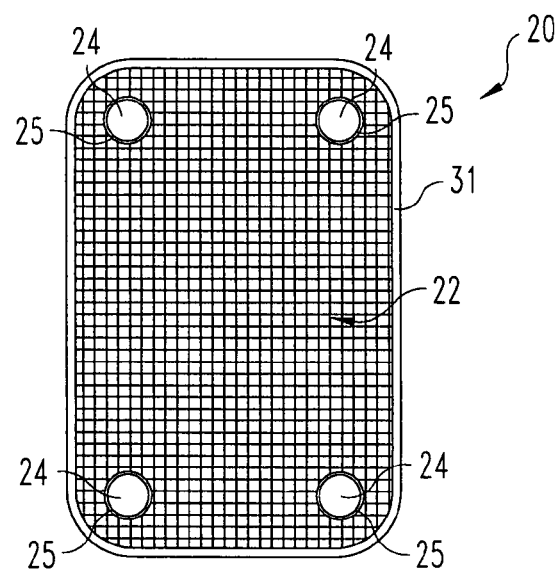
FIG. 3 is a plan view of a ligament implant according to one embodiment of the present invention.

Referring now to FIG. 3, one embodiment of an implant made from the mesh material of the present invention is illustrated. Implant 20 has a mesh portion 22 having a generally rectangular or square shape. In the illustrated embodiment, the mesh portion is bounded by a reinforcing band 31. Mesh portion 22 has a number of holes 24 therethrough through which fasteners may be placed to secure implant 20 to bone or other tissue of a patient. Grommets 25 or other reinforcing material may be placed around holes 24 to reinforce the holes and provide secure gripping between the fasteners and mesh portion 22. The fasteners can for the implants of the present invention include screws, staples, sutures, tacks and the like, which may or may not be formed of metallic materials. Furthermore bone adhesives such as calcium phosphate, polymethacrylate and the like can be used with the implants of the present invention. In one specific application, implant 20 can be used to replace the resected portion of the anterior longitudinal ligament removed during insertion of one or more interbody fusion devices into an intervertebral disc space from an anterior approach. Implant 20 can be secured to the vertebral bodies on each side of the subject disc space. It is further contemplated that the width of implant 20 could be reduced and a single hole 24 provided at each end of implant 20. Such a reduced width implant 20 could have application to replace other ligament structures associated with the spinal column or other ligaments in the body. The bone or tissue growth material formed with the mesh portion promotes growth of a replacement ligament and incorporation of implant 20 into the body tissue.

Figure 4:
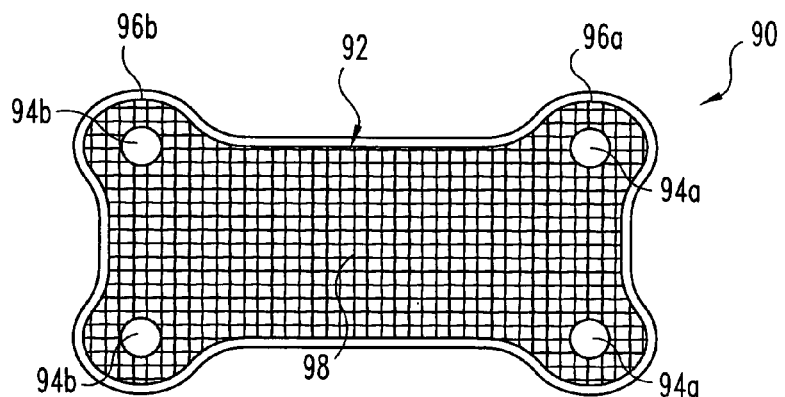
FIG. 4 is a plan view of a bone plate implant according to another embodiment of the present invention.

Referring now to FIG. 4, another embodiment implant made from the mesh material of the present invention is illustrated. Implant 90 is provided in the form of a bone plate having a mesh portion 92. Mesh portion 92 has holes 94a, 94b formed therethrough to accommodate screws or other bone engaging fasteners at the enlarged ends 96a, 96b, respectively of the implant 90. In the illustrated embodiment, the middle portion of implant 90 has a reduced width mid-portion 98 to reduce intrusion of implant 90 into the surrounding tissue and vasculature. Implant 90 could have application as a bone plate that extends across a bone fracture and is secured to the adjacent bony sections. Implant 90 could also have application as an anterior, or anterolateral, or lateral spinal column plate that extends across a disc space and is secured to the adjacent vertebral other reinforcing material may be placed around holes 24 to reinforce the holes and provide secure gripping between the fasteners and mesh portion 22. The fasteners can for the implants of the present invention include screws, staples, sutures, tacks and the like, which may or may not be formed of metallic materials. Furthermore bone adhesives such as calcium phosphate, polymethacrylate and the like can be used with the implants of the present invention. In one specific application, implant 20 can be used to replace the resected portion of the anterior longitudinal ligament removed during insection of one or more interbody fusion devices into an intervertebral disc space from an anterior approach. Implant 20 can be secured to the vertebral bodies on each side of the subject disc space. It is further contemplated that the width of implant 20 could be reduced and a single hole 24 provided at each end of implant 20. Such a reduced width implant 20 could have application to replace other ligament structures associated with the spinal column or other ligaments in the body. The body or tissue growth material formed with the mesh portion promotes growth of a replacement ligament and incorporation of implant 20 into the body tissue.

Referring now to FIG. 4, another embodiment implant made from the mesh material of the present invention is illustrated. Implant 90 is provided in the form of a bone plate having a mesh portion 92. Mesh portion 92 has holes 94a, 94b formed therethrough to accomodate screws or other bone engaging fasteners at the enlarged ends 96a, 96b, respectively of the implant 90. In the illustrated embodiment, the middle portion of implant 90 has a reduced width mid-portion 98 to reduce intrusion of implant 90 into the surrounding tissue and vasculature. Implant 90 could have application as a bone plate that extends across a bone fracture and is secured to the adjacent bony sections. Implant 90 could also have application as an anterior, or anterolateral, or lateral spinal column plate that extends across a disc space and is secured to the adjacent vertebral bodies. Tissue growth material formed with the mesh portion promotes bone growth and fusion and incorporation of implant 90 into the body tissue.

Figure 5A:
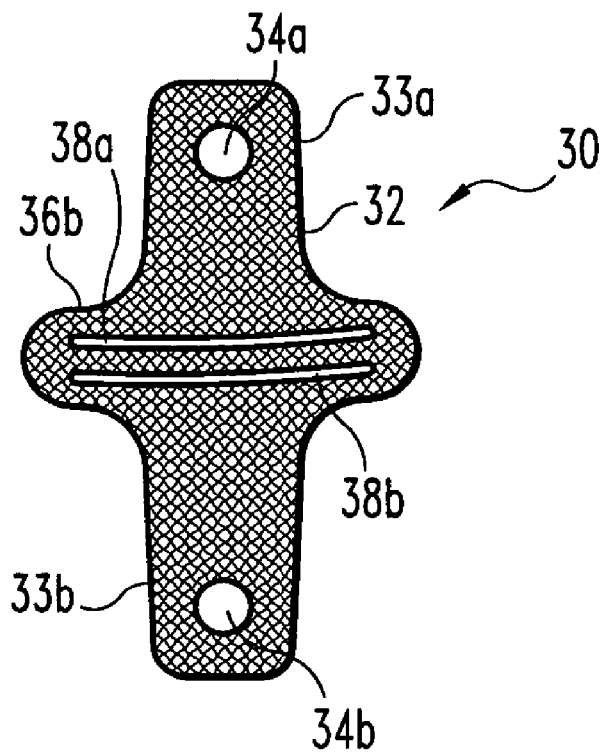
FIGS. 5(a) and 5(b) are an elevational view and a top plan view, respectively, of an annulus repair and ligament implant according to a further embodiment of the present invention.
Figure 5B:
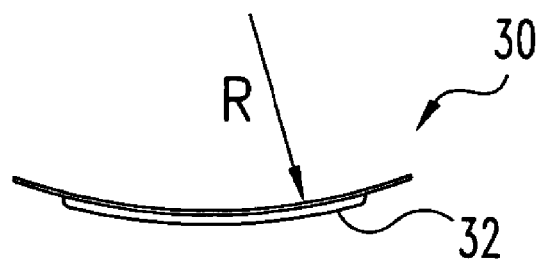

Referring now to FIGS. 5(a) and 5(b), a further embodiment implant made from the mesh material of the present invention is illustrated. Implant 30 has application as a prosthetic ligament or a tension band and annulus repair device. Implant 30 has mesh portion 32 with holes 34a, 34b formed in each of the longitudinally extending sections 33a, 33b, respectively. Implant 30 further has laterally extending sections 36a and 36b. One or more reinforcing elements such as rods or spars 38a and 38b can be embedded in or attached to the exterior of mesh portion 32. In the embodiment of FIGS. 5(a) and 5(b), spars 38a, 38b extend horizontally between the laterally extending portions 36a, 36b although the spars may be oriented in a number of different directions. Spars 38a, 38b act to reinforce and provide additional stiffness to mesh portion 32. As shown in FIG. 5(b), mesh portion 32 is curved along a radius R in order to conform to the original shape of the disc space annulus and the adjacent vertebral bodies. It is further contemplated that spars 38a and 38b could be stiff metal or plastic rods and/or could be bendable to allow implant 30 to be custom shaped to the annulus and vertebral bodies and to maintain mesh portion 32 in the desired curvature.

In preferred embodiments, spars 38a, 38b are provided to exhibit greater resistance to deformation than that exhibited or observed for a fiber or a finite number of bundled fibers preferably a greater resistance to deformation than a bundle exceeding 10 fibers, still yet more preferably exceeding a bundle of 15 fibers. The individuals spars 38a, 38b can be formed of the same material as the fibers or a different material. If the spars 38a, 38b are formed of the same or similar material as the fibers, the spars 28a, 38b can be thicker and/or heated treated to increase the material strength. Alternatively, the spars can be formed of a different, harder material than the fibers. In one form, the spar exhibits greater tensile strength than the fibers. The spars can induce substantial inelasticity into the implant. The spars can be formed of a shape memory polymeric material, or metal or metal alloy similar to those forming the fibers or the spar can be formed of a shape memory metallic alloy such as NITINOL®.

The spar(s) can be connected or attached to the fibers by a wide variety of methods and materials. Typically the spar(s) will be attached to two or more fibers using the same or similar methods and materials that interconnect the fibers. Although it should be understood that in selected implants the methods/materials used to interconnect the plurality of fibers need not be the same methods/materials used to connect the spar(s) to the fibers.

Figure 6:
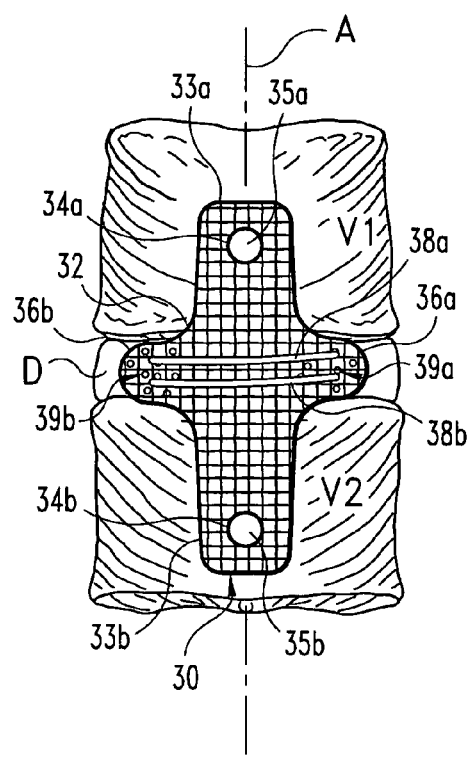
FIG. 6 is an elevational view of the annulus repair and ligament implant of FIGS. 5(a) and 5(b) attached to an annulus and the adjacent vertebrae.

As shown in FIG. 6, bone engaging fasteners 35a and 35b attach longitudinally extending portions 33a, 33b of implant 30 to vertebra V1 and vertebra V2, respectively. Annulus engaging fasteners 39a, 39b, such as sutures or staples, can be used to attach laterally extending portions 36a, 36b to the annulus surrounding disc space D. It is contemplated that implant 30 can be used in any number of orthopedic applications, such as repair of anterior longitudinal ligaments following anterior intervertebral disc surgery, anterior longitudinal ligament restoration, or to repair the annulus following microdiscectomy surgery or implant insertion in the disc space D. Tissue growth material formed with the mesh portion promotes tissue growth and repair of the annulus.

Figure 7:
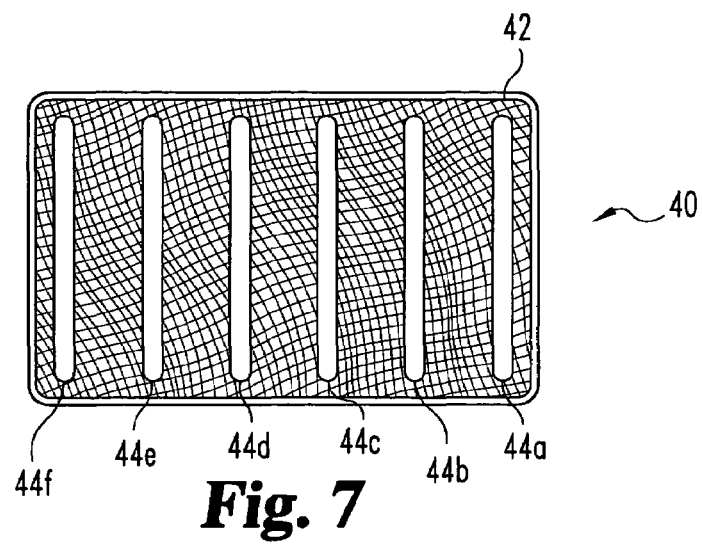
FIG. 7 is a plan view of a stabilization implant according to another embodiment of the present invention.
Figure 8:
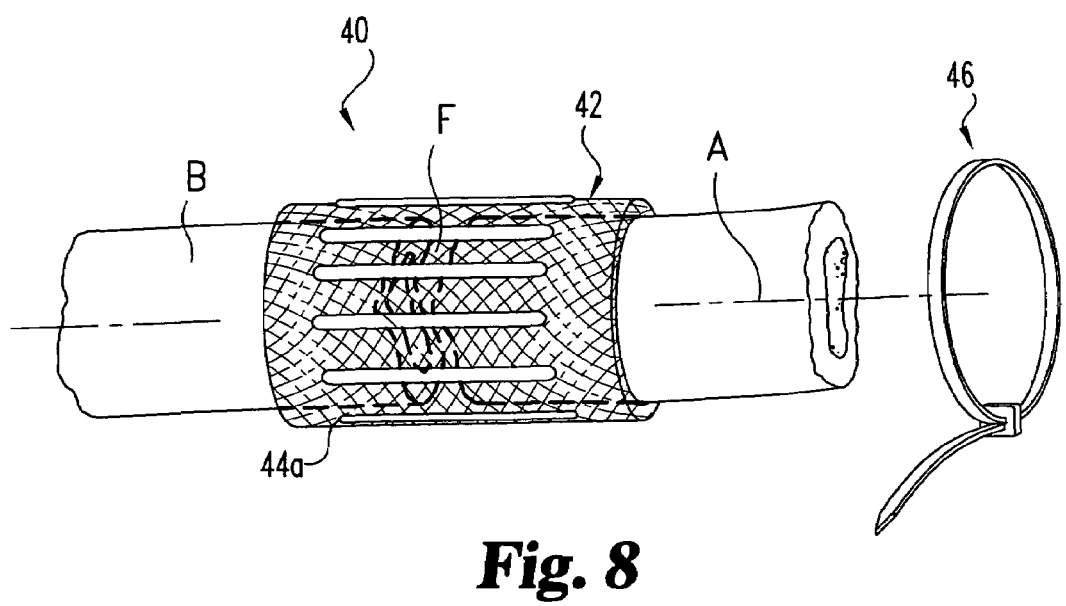
FIG. 8 is an elevational view of the implant of FIG. 7 wrapped around a bone defect.

Referring now to FIG. 7, yet a further embodiment implant made from the mesh material of the present invention is illustrated. Implant 40 has a generally rectangular mesh portion 42 with a number of spars 44a, 44b, 44c, 44d, 44e, and 44f secured thereto as discussed above with respect to implant 30. Implant 40 has one specific application for repair of a fracture F in bone B as shown in FIG. 8. Implant 40 can be provided to form an annulus. For example, implant 40 can be wrapped around bone B such that spars 44 extend along the axis A of the bone B and across the fracture F. Implant 40 can be secured to bone B by placing one or more surgical fixation devices 46, such as a SONGER cable, around the implant 40. It is also contemplated that wires, screws, sutures, anchors, staples or other fastening devices can be used to secure implant 40 to bone B to immobilize fracture F. Alternatively, one ore more spars 44a-44f can be provided to conform the implant about the bone B, particularly a bone defect. The spars 44a-44f can be pre-formed. Alternatively, spars 44a-44f can be formed of a deformable or shape memory material adapted to conform to or bear against bone B. Tissue growth material formed with the mesh portion promotes tissue growth and incorporation into the body tissue.

Figure 9:
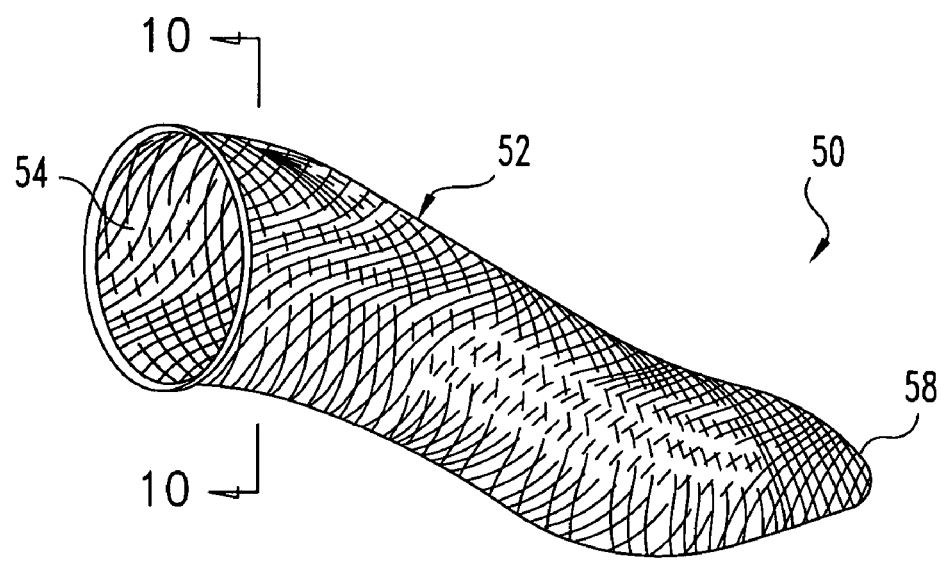
FIG. 9 is a perspective view of one embodiment of a hollow implant according to another form of the present invention.
Figure 10:
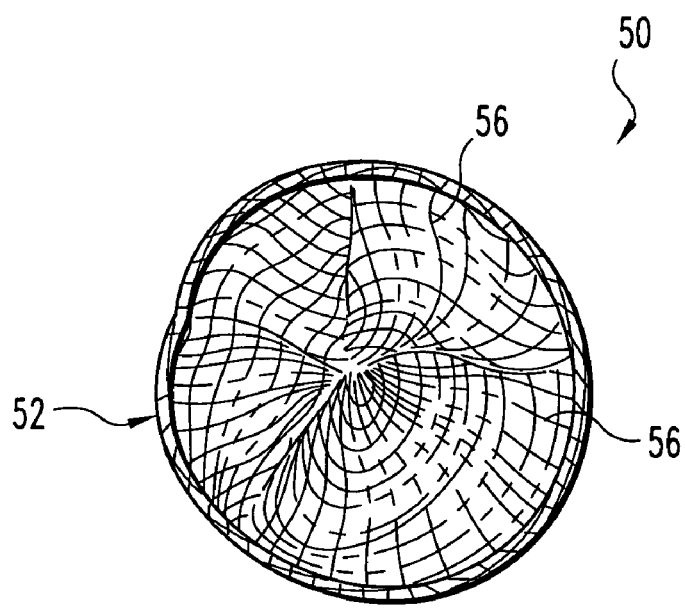
FIG. 10 is a sectional view taken through line 10-10 of FIG. 9.

The mesh material of the present invention also has application with bags or other devices capable of holding various curing materials that are to be inserted internally to repair a fracture or to span a joint, such as between vertebrae. For example, in FIG. 9 there is illustrated a tubular structure 50 that includes a mesh portion 52 having a generally cylindrical shape. Mesh portion 52 has an end opening 54 through which curable material could be placed and an opposite closed end 58. As shown in FIG. 10, multiple single wire strands 56 extend across and interconnect the walls of mesh portion 52. Curing material, such as polymethylmethacrylate, calcium sulfate, calcium phosphate, or liquid silicone can be placed or injected through end opening 54 and into the hollow interior of implant 50. The curing material can be either in its initial form or in its cured form either an amorphous material or a crystalline or substantially crystalline material. The material as it cures can develop a pressure internally in implant 50, and internal wires 56 become stressed radially outwardly. The spars, if included, can further support the wire stands and/or resist over deformation induced by the curing material. When the injected material hardens, the residual stress formed in wires 56 (and optionally in the spars) applies a compressive force to the injected, cured material.

The mechanical properties of the injected material can be altered to meet design parameters by varying the properties of the wire reinforcement. Examples of parameters that can be varied include the diameter of the wire, the number of wires, direction of the wires, and injection pressure for the curing material. The surface finish of the wire can also be treated to alter the surface interactive properties of the wire in relation to the injected material. For example, the wire can be provided with a coating or a thermal treatment in order to alter specific properties. The tissue growth/bone growth material used with implant 50 promotes bone growth and fusion and incorporation of implant 50. Also the external surface of the implant fibers treated with a bone cement to secure the implant to a selected bone or tissue structure.

Figure 11:
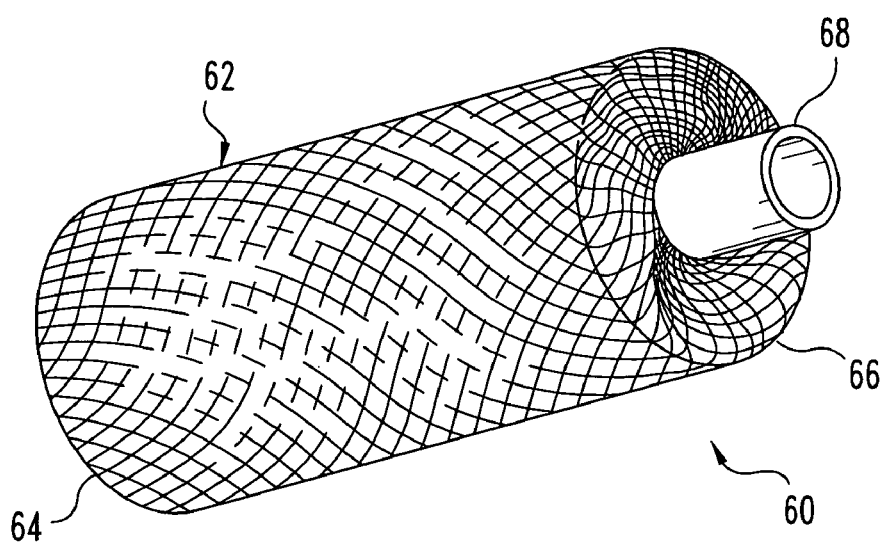
FIG. 11 is a perspective view of another embodiment hollow implant according to the present invention.

Referring now to FIG. 11, another embodiment hollow implant formed with mesh material of the present invention is illustrated. Implant 60 has a mesh wall portion 62 that defines a hollow interior. Implant 60 further has a first end 64 and an opposite second end 66. An injection port 68 is provided at second end 66. Curable material is injectable through port 68 and into the hollow interior of implant 60 using various injection devices. For example, a syringe, catheter or the like can be used. In selected embodiments a commercially available injection device, sold under the trade name PARALLAX or similar device can be used with the present invention. Once implant 60 is filled with material and the material is cured, then implant 60 is substantially incompressible and capable of supporting compressive loads. Implant 60 can be provided with a detachable cap that is attachable to port 68 after material is injected into implant 60. Alternatively implant 60 can include one or more self-sealing ports that allow influx of a curable material but prevent leakage of the curing/cured material even under the extreme compressive loads excerpted by the spinal column. Implant 60 has application as an interbody spinal fusion device that can be inserted singly or in side-by-side relation with a second implant 60 into a spinal disc space in order to support the spinal column and facilitate fusion between the adjacent vertebral bodies. It is further contemplated that implant 60 could be inserted into the interior of a bone for fracture repair. The tissue/bone growth material used with implant 60 promotes bone growth along with fusion and incorporation of implant 60.

Figure 12:
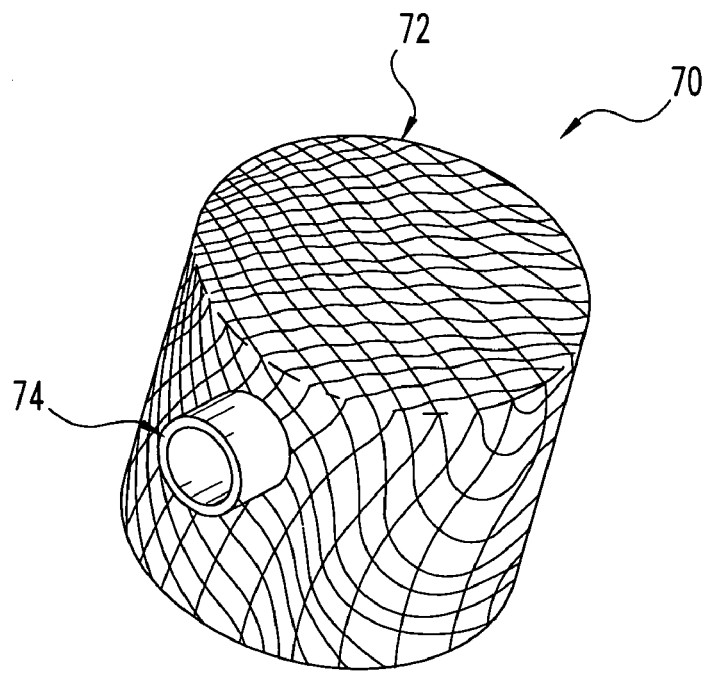
FIG. 12 is a perspective view of yet another embodiment hollow implant according to the present invention.

As shown in FIG. 12, another embodiment of a hollow implant made with the mesh material of the present invention is shown. Implant 70 has a mesh wall portion 72 defining a hollow interior and an injection port 74. Implant 70 has upper and lower surfaces that have a shape that allows these surfaces to occupy a substantial area of the vertebral endplates. Implant 70 further has a height between these upper and lower surfaces that allows the normal disc space height to be restored. One or more implants 70 could be inserted into a spinal disc space. The tissue/bone growth material used with implant 70 promotes bone growth along with fusion and incorporation of implant 70.

Figure 13:
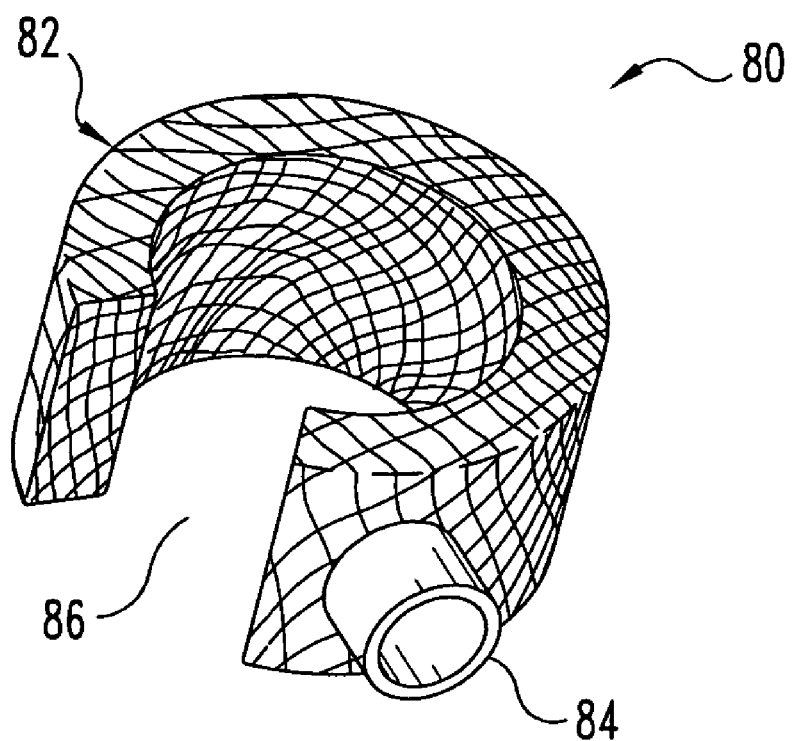
FIG. 13 is a perspective view of a further embodiment hollow implant according to the present invention.

Referring now to FIG. 13, another embodiment hollow implant made with the mesh material of the present invention is illustrated. Implant 80 has mesh wall portion 82 defining an interior cavity into which curable material may be injected through a port 84. Implant 80 has C-shape or other generally annular shape defining a holding area 86. A bone graft can be positioned in holding area 86 before or after implant 80 is filled with material. The tissue/bone growth material used with implant 80 promotes bone growth along with fusion and incorporation of implant 80 along with the bone graft.

While the invention has been illustrated and described in detail in the drawings and foregoing description, the same is to be considered as illustrative and not restrictive in character, it being understood that only the illustrated embodiments have been shown and described, and that all changes and modifications that come within the spirit of the invention are desired to be protected.

What is claimed is:

1. An orthopedic implant comprising:
   an interconnecting network of flexible and deformable metallic fibers configured to conform to a selected bone structure;
   one or more reinforcing elements comprising a reinforcing band secured to and bounding an entire outer perimeter of said network of metallic fibers to provide the orthopedic implant with a low profile, sheet-like structure having a substantially planar configuration;
   one or more bone fasteners extending through the network or one of the reinforcing elements;
   an osteogenic material impregnating at least a portion of the interconnecting network between said metallic fibers to promote bone growth into said network of metallic fibers, wherein said implant is adapted for promoting fusion between adjacent bone structures; and
   wherein the sheet-like structure is sized to extend across a space between the adjacent bone structures and includes opposite end portions, at least one of the bone fasteners extending through each of the opposite end portions to secure the sheet-like structure to the adjacent bone structures.

2. The implant of claim 1 adapted to secure to at least two adjacent vertebral bodies to promote spinal fixation.

3. The implant of claim 1 wherein the reinforcing band extends continuously about the outer perimeter of the interconnecting network of metallic fibers.

4. The implant of claim 1 wherein the reinforcing elements are formed of a material selected from the group consisting of: stainless steel, cobalt-chrome alloy, titanium, titanium alloy, or nickel-titanium shape memory alloys, biocompatible polymeric materials, nylon fibers, carbon fibers, glass fibers, collagen fibers, ceramic fibers, polyethylene fibers, poly(ethylene terephthalate), polyglycolides, polylactides, and combinations thereof.

5. The implant of claim 1 wherein the fibers are composed of a material selected from the group consisting of: stainless steel, cobalt chrome alloys, titanium, titanium alloys, and nickel titanium alloys.

6. The implant of claim 1 wherein a pair of the bone fasteners extends through at least one of the opposite end portions of the sheet-like structure to secure the sheet-like material to the adjacent bone structure.

7. The implant of claim 1 wherein the interconnecting network of metallic fibers includes at least two openings extending therethrough for receiving corresponding ones of the bone fasteners; and further comprising a reinforcing member positioned about each of the openings to reinforce the openings extending through the interconnecting network of metallic fibers.

8. The implant of claim 7 wherein the reinforcing member comprises a grommet.

9. The implant of claim 1 wherein the metallic fibers are woven together to form an interwoven network of metallic fibers.

10. The implant of claim 1 wherein the bone fasteners are positioned through respective openings in the network of metallic fibers to secure the sheet-like structure to the adjacent bone structures.

11. An orthopedic implant comprising:

a network composed of a plurality of flexible and deformable metallic fibers, one or more reinforcing elements comprising a reinforcing band secured to and bounding an entire outer perimeter of said network of metallic fibers to provide the orthopedic implant with a low profile, sheet-like structure having a substantially planar configuration, said reinforcing elements formed of a bendable material configured to conform the network to a selected bone structure;

one or more bone fasteners extending through the network or through the one or more reinforcing elements; and an osteogenic material impregnating at least a portion of the network between said metallic fibers to promote bone growth into said network of metallic fibers; and wherein the sheet-like structure is sized to extend across a space between adjacent bone structures and includes opposite end portions, at least one of the bone fasteners extending through each of the opposite end portions to secure the sheet-like structure to the adjacent bone structures.

12. The implant of claim 11 wherein the reinforcing band extends continuously about the outer perimeter of the network of metallic fibers.

13. The implant of claim 11 wherein a pair of the bone fasteners extends through at least one of the opposite end portions of the network of metallic fibers to secure the network of metallic fibers to the adjacent bone structure.

14. The implant of claim 11 wherein the network of metallic fibers are woven together to form an interwoven network of metallic fibers.

15. The implant of claim 11 wherein the bone fasteners are positioned through respective openings in the network of metallic fibers to secure the sheet-like structure to the adjacent bone structures.

16. An orthopedic implant comprising:

an interconnected network of flexible and deformable metallic fibers;

one or more reinforcing elements comprising a reinforcing band secured to and bounding an entire outer perimeter of the interconnected network of metallic fibers to provide the orthopedic implant with a low profile, sheet-like structure having a substantially planar configuration;

at least two bone fasteners; and an osteogenic material impregnating at least a portion of the interconnected network between said metallic fibers to promote bone growth into said network of metallic fibers; and wherein the sheet-like structure is sized to extend across a space between adjacent bone structures and includes opposite end portions, at least one of the bone fasteners extending through each of the opposite end portions to secure the sheet-like structure to the adjacent bone structures.

17. The implant of claim 16 wherein a pair of the bone fasteners extends through at least one of the opposite end portions to secure the sheet-like structure to the adjacent bone structure.

18. The implant of claim 17 wherein a pair of the bone fasteners extends through each of the opposite end portions to secure the sheet-like structure to the adjacent bone structures.

19. The implant of claim 16 wherein each of the opposite end portions defines an opening extending therethrough for receiving a corresponding one of the bone fasteners to secure the sheet-like structure to the adjacent bone structures.

20. The implant of claim 19 wherein at least one of the opposite end portions defines a pair of the openings extending therethrough for receiving a corresponding pair of the bone fasteners to secure the sheet-like structure to the adjacent bone structure.

21. The implant of claim 16 wherein the interconnected network of metallic fibers includes at least two openings extending therethrough for receiving corresponding ones of the bone fasteners to secure the opposite end portion of the sheet-like structure to the adjacent bone structure; and further comprising a reinforcing member positioned about each of the openings to reinforce the openings extending through the interconnected network of metallic fibers.

22. The implant of claim 21 wherein the reinforcing member comprises a grommet.

23. The implant of claim 16 wherein the metallic fibers are woven together to form an interwoven network of metallic fibers.

24. The implant of claim 16 wherein the bone fasteners are positioned through respective openings in the network of metallic fibers to secure the sheet-like structure to the adjacent bone structures.

* * * * *